US012708780B2

(12) United States Patent
Hoffman et al.

(10) Patent No.: US 12,708,780 B2
(45) Date of Patent: Aug. 18, 2026

(54) DETERMINATION OF LOWER PACING RATE LIMIT

(71) Applicant: Medtronic, Inc., Minneapolis, MN (US)

(72) Inventors: Matthew J. Hoffman, St. Paul, MN (US); Troy E. Jackson, Rogers, MN (US); Markus Meyer, Williston, VT (US)

(73) Assignee: Medtronic, Inc., Minneapolis, MN (US)

( * ) Notice: Subject to any disclaimer, the term of this patent is extended or adjusted under 35 U.S.C. 154(b) by 388 days.

(21) Appl. No.: 18/138,686

(22) Filed: Apr. 24, 2023

(65) Prior Publication Data

US 2023/0347154 A1 Nov. 2, 2023

Related U.S. Application Data

(60) Provisional application No. 63/336,783, filed on Apr. 29, 2022.

(51) Int. Cl.
*A61N 1/365* (2006.01)
*A61N 1/372* (2006.01)

(52) U.S. Cl.
CPC ...... *A61N 1/36592* (2013.01); *A61N 1/37235* (2013.01)

(58) Field of Classification Search
CPC .. A61N 1/362; A61N 1/3627; A61N 1/36592; A61N 1/37235; A61N 1/39
See application file for complete search history.

(56) References Cited

U.S. PATENT DOCUMENTS

| | | | | |
|---|---|---|---|---|
| 4,945,909 | A | 8/1990 | Fearnot et al. | |
| 4,972,834 | A | 11/1990 | Begemann et al. | |
| 5,814,087 | A | 9/1998 | Renirie | |
| 5,861,011 | A | 1/1999 | Stoop | |
| 6,650,937 | B2 | 11/2003 | Kerver | |
| 6,975,903 | B1 | 12/2005 | Min et al. | |
| 7,155,280 | B2 | 12/2006 | Daum et al. | |
| 8,190,256 | B2 * | 5/2012 | Hartley ................ | A61B 5/4812 607/9 |
| 8,352,027 | B2 | 1/2013 | Spinelli | |
| 8,831,721 | B2 | 9/2014 | Hettrick et al. | |
| 9,339,231 | B2 | 5/2016 | Thakur et al. | |
| 9,630,001 | B2 | 4/2017 | Kronberg et al. | |

(Continued)

FOREIGN PATENT DOCUMENTS

WO 2018/017900 1/2018

OTHER PUBLICATIONS

International Search Report and Written Opinion for PCT/US2023/019822 dated Jan. 12, 2024 (27 pages).

*Primary Examiner* — Brian T Gedeon
(74) *Attorney, Agent, or Firm* — Mueting Raasch Group

(57) ABSTRACT

A lower pacing rate limit is utilized by pacing devices to initiate pacing in response to a patient's intrinsic rate being less than the lower pacing rate limit. Illustrative systems, devices, and methods may obtain rate modification information related to a patient such as physical characteristics, diagnostic parameters, pathologies, device characteristics of a pacing device implanted in the patient, and patient-reported information. The rate modification information may be used to determine lower pacing rate limit based thereon.

33 Claims, 8 Drawing Sheets

(56) References Cited

U.S. PATENT DOCUMENTS

| | | | | |
|---|---|---|---|---|
| 9,682,240 | B2 | 6/2017 | Hettrick et al. | |
| 10,058,708 | B2 | 8/2018 | Inman et al. | |
| 10,182,729 | B2 | 1/2019 | Zielinski et al. | |
| 2002/0120305 | A1* | 8/2002 | Sun | A61N 1/36542 607/19 |
| 2005/0010254 | A1* | 1/2005 | Zhang | A61B 5/33 607/9 |
| 2012/0108984 | A1* | 5/2012 | Bennett | A61B 5/0022 705/2 |
| 2016/0174904 | A1* | 6/2016 | Thakur | A61B 5/7282 600/528 |
| 2017/0056664 | A1 | 3/2017 | Kane | |
| 2018/0344212 | A1* | 12/2018 | An | A61B 5/053 |

* cited by examiner

DETERMINATION OF LOWER PACING RATE LIMIT

This application claims the benefit of U.S. Provisional Pat. App. Ser. No. 63/336,783 entitled "Determination of Lower Pacing Rate Limit" filed on Apr. 29, 2022, which is incorporated by reference herein in its entirety.

This disclosure generally relates to determination of a lower pacing rate limit for use in pacing devices.

Pacing devices, such as implantable medical devices (IMDs), may utilize a lower pacing rate limit to determine when to initiate pacing. For instance, IMDs may trigger, or initiate, the delivery of pacing in response to the patient's intrinsic heart rate being less than the lower pacing rate limit. In other words, when a patient's intrinsic heart rate moves below the lower pacing limit, IMDs may begin delivering pacing at the lower pacing limit. The lower pacing rate limit of the pacing devices is programmed during initial configuration of the pacing devices after implantation, and often the lower pacing rate limit is not changed after the initial programming. Additionally, the lower pacing rate limit is also typically unchanged from the default rate, which is often 60 beats per minute, during initial configuration. Moreover, selection of the lower pacing rate limit, for instance, by a physician may not be guided by factors or evidence.

Additionally, various cardiac pathologies may provide insight into an optimal, or more therapeutic, lower pacing rate limit. For example, patients with systolic dysfunction may benefit from pacing at low rates than patients with diastolic dysfunction or heart failure with a preserved ejection fraction (HFpEF). Human clinical evidence shows promise in an elevated lower pacing rate limit in HFpEF patients.

SUMMARY

The techniques of this disclosure generally relate to determination, or generation, of lower pacing rate limit for use in pacing devices. The determination, or generation, may be based on one or more different pieces of rate modification information. For example, the rate modification information may include physical characteristics of a patient such as height, sex, age, body mass index (BMI), body surface area, physical fitness level, and activity level. Further, for example, the rate modification information may include diagnostic parameters of a patient such as ventricular contractility, ventricular stiffness, pulse transit time, resting heart rate, nighttime heart rate, arrhythmia burden, targeted pacing burden, heart rate recovery, impedance, fluid overload, respiration rate, maximum heart rate, ejection fraction, left ventricular pressure, comorbid disease, systemic blood pressure, pulmonary artery pressure, blood oxygenation, and presence or concentration of serum biomarkers. Further, for example, the rate modification information may include pathologies of a patient such as diastolic dysfunction/heart failure with preserved ejection fraction, systolic dysfunction, chronotropic incompetence, and worsening heart failure. Still further, for example, the rate modification information may include pacing device configurations such as pacing electrode locations and pacing therapy type. Additionally, further rate modification information may be provided by users such as the patients themselves. The patients may provide input or preferences based on objective and subjective observations of themselves.

One or more of such pieces of rate modification information may be utilized by the illustrative systems, methods, and devices described herein to determine (e.g., generate, calculate, etc.) a lower pacing rate limit. In one or more embodiments, a physician may utilize, or use, an illustrative system that determines the lower pacing rate limit. Such illustrative system may obtain, or acquire, the rate modification information from a variety of sources including user input dialogs on a local system for use by a physician or technician, local or remote computing devices (e.g., electronic medical records systems), data measured or monitored by one or more medical devices including the pacing device, user input dialogs on a mobile computing device for use by patients, etc. Then, the illustrative system may utilize such rate modification information to determine the lower pacing rate limit for the patient. Additionally, in one or more embodiments, after implant, the pacing device itself may measure, or monitor, rate modification information from the patient, and modify, or change, the lower pacing rate limit based on the measured, or monitored, rate modification information.

Further, physicians may provide input or preferences based on their knowledge of a patient and the patient's condition that may be used in conjunction with the rate modification information. For example, physicians may provide a lower bound and an upper bound. When the illustrative systems, devices, methods, and processes determine, or generate, the lower pacing rate limit, the physician input upper and lower bounds may be utilized to ensure that the lower pacing rate limit is not less than the lower bound nor greater than the upper bound. Additionally, physicians may provide a percentage of pacing desired, which may be used by the IMDs to increase the lower pacing rate limit if a patient is exceeding the percentage of pacing desired during therapy. For instance, if the lower pacing rate limit is set to 70, 95% of the hearts beats are paced, and the physician input percentage of pacing desired is 90%, the lower pacing rate limit may be increased (e.g., incrementally) until percentage of heart beats that are paced is equal to or less than the percentage of pacing desired.

The illustrative systems, devices, methods, and processes may be described as assisting clinician in determining the optimal lower pacing rate limit, which may increase the likelihood that the device lower pacing rate limit is programmed optimally. Additionally, the illustrative methods and processes may be described as features that are incorporated into illustrative device programming instruments and systems to help facilitate the programming of a patient-specific lower pacing rate limit. Further, the illustrative technology may be further described as a tool, or algorithm, for optimizing a programmed lower pacing rate limit, or lower rate setting, on devices with cardiac pacing capability.

The illustrative methods, and processes may be incorporated in a programming instrument or networked system and may be described as calculating a lower pacing rate limit based on a variety of data sources, including data manually entered or from connected databases. Further, the illustrative systems, devices, methods, and process may be described as utilizing device diagnostic data and patient self-reported data to adjust the lower pacing rate limit over time to optimize for clinical outcome and/or reduction of symptoms. Further, the illustrative systems, devices, methods, and processes may be described as assisting in the selection of an optimal lower pacing rate limit thereby reducing clinical burden in identifying programming best-practices. One illustrative embodiment may be described as an application on programming instrument or networked system that calculates a lower pacing rate limit based on patient-specific rate modification information such as, e.g., patient height, sex, age, pathology, lead location, and desired activity performance. The rate modification information can be entered manually such, e.g., at the time of initial programming on a programmer instrument, and/or could be imported from other connected data sources/registries (e.g., electronic medical records) to calculate the lower pacing rate limit. Another illustrative embodiment may be an IMD that refines the programmed lower pacing rate limit based on rate modification information that is monitored, or measured, over time using the IMD or other connected patient monitor devices itself. For example, lower pacing rate limit may be increased or decreased based on pre-specified targets of one or more diagnostic parameters such as, e.g., targeted pacing burden, arrhythmia burden, nighttime heart rate, activity, etc. Another illustrative embodiment may utilize patient-reported information is obtained from a mobile computing device. For instance, this embodiment may adjust the lower pacing rate limit for patient symptoms within a pre-specified range. The patient-reported information (e.g., patient-reported symptoms) may be provided using a patient mobile application on a mobile computing device, such as a cellular smartphone. The mobile computing device and/or the IMD communicatively coupled thereto may adjust the lower pacing rate limit to attempt to minimize the patient-reported symptoms such, e.g., energy level, peripheral edema, etc.

In one example, aspects of this disclosure relate to determining a lower pacing rate limit where the lower pacing rate limit is utilized by the pacing device to initiate pacing in response to the patient's intrinsic rate being less than the lower pacing rate limit. One illustrative method may include obtaining rate modification information comprising at least one physical characteristic of a patient utilizing a pacing device and determining a lower pacing rate limit for the pacing device based on the obtained rate modification information.

One illustrative system may include a computing apparatus comprising one or more processors. The computing apparatus may be configured to obtain rate modification information comprising at least one physical characteristic of a patient utilizing a pacing device and determine a lower pacing rate limit for the pacing device based on the obtained rate modification information, One illustrative implantable medical device may include one or more electrodes to deliver cardiac pacing therapy to and sense electrical activity from a patient's heart and a computing apparatus operably coupled the one or more electrodes and comprising one or more processors. The computing apparatus of the implantable medical device may be configured to monitor the patient's intrinsic heart rate using the one or more electrodes, deliver pacing therapy to the patient's heart in response to the patient's intrinsic rate being less than a lower pacing rate limit, obtain rate modification information comprising at least one physical characteristic of a patient utilizing a pacing device, and determine a lower pacing rate limit for the pacing device based on the obtained rate modification information.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The techniques of this disclosure generally relate to determination of lower pacing rate limit for use in pacing devices. Pacing devices, such as implantable medical devices (IMDs), may utilize a lower pacing rate limit to determine when to initiate pacing. In particular, pacing devices may imitate, or deliver, pacing therapy in response to the patient's intrinsic rate being less than the lower pacing rate limit. In other words, the lower pacing rate limit may be described as being a rate at which the pacing devices pace the patient's heart in absence of intrinsic cardiac activity. Illustrative systems, devices, methods, and processes that determine and/or adjust the lower pacing rate limit are described herein with respect to FIGS. 1-7.

Figure 1:
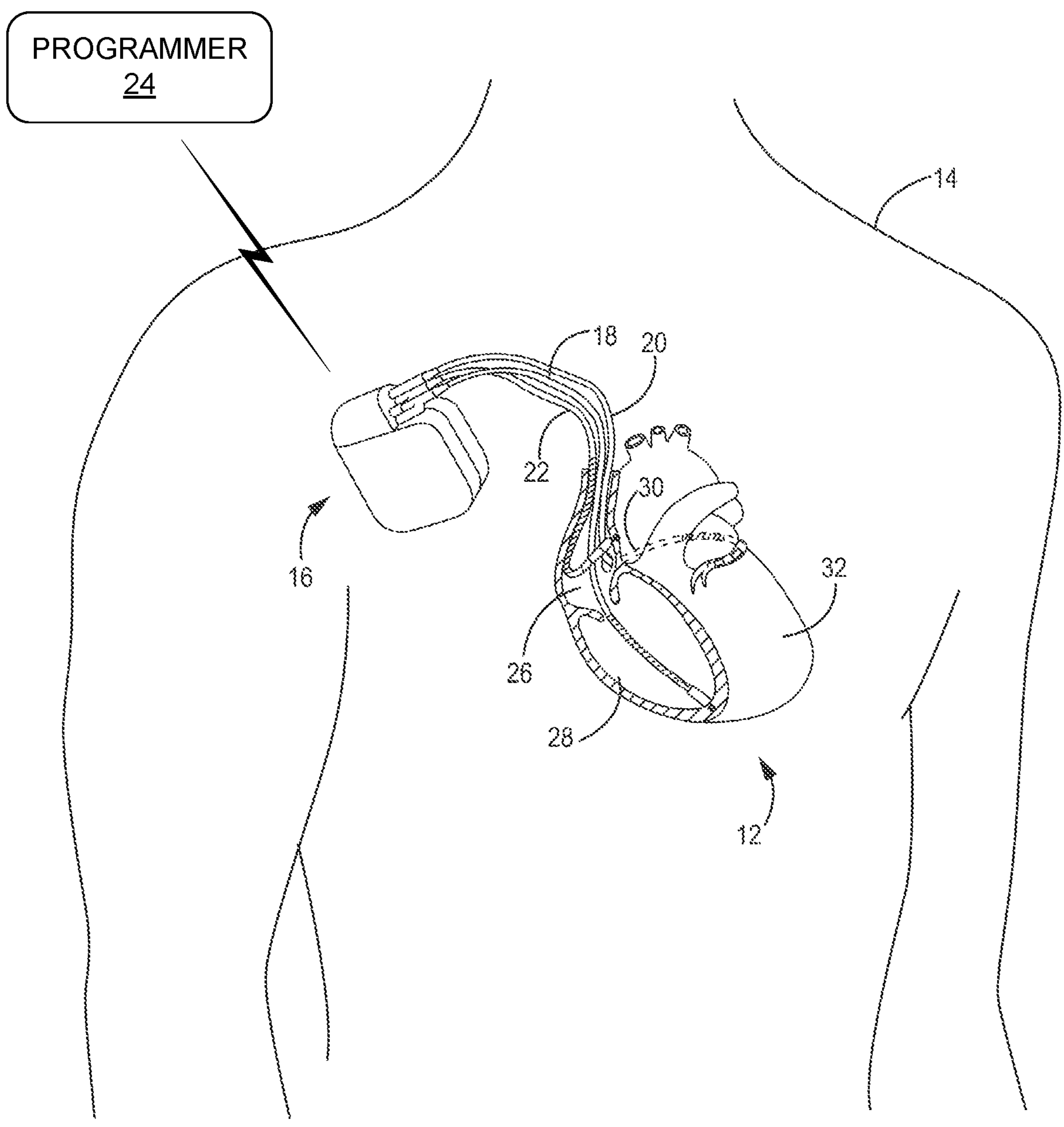
FIG. 1 is a diagram of an illustrative system including an IMD and a programmer.

FIG. 1 is a conceptual diagram of an exemplary therapy system 10 that may be used to deliver pacing therapy, such as adaptive cardiac pacing therapy, cardiac resynchronization therapy, etc., to a patient 14. While patient 14 is shown as a human, patient 14 may also be a variety of other types of animals. The therapy system 10 may include an implantable medical device 16 (IMD), which may be coupled to leads 18, 20, 22, and programmer 24. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pacing rate, R-R interval, A-V delay and other various timings, pulse width, amplitude, voltage, burst length, etc. Further, the IMD 16 may be operable to use various electrode configurations to deliver pacing therapy, which may be unipolar, bipolar, quadripolar, or further multipolar. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD, or electrode apparatus. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of the heart 12 is stopped.

In some examples, the programmer 24 may be a mobile computing device or a computer workstation. The programmer 24 may include a user interface that receives input from a user. The user interface may include, for example, a keypad and a display, which may, for example, be a liquid crystal display (LCD) or light emitting diode (LED) display. The keypad may take the form of an alphanumeric keypad or a reduced set of keys associated with particular functions. The programmer 24 can additionally or alternatively include a peripheral pointing device, such as a mouse, via which a user may interact with the user interface. In some embodiments, a display of the programmer 24 may include a touch screen display, and a user may interact with the programmer 24 via the display.

A user, such as a physician, technician, patient, or other user, may interact with the programmer 24 to communicate with the IMD 16. For example, a user may interact with the programmer 24 to retrieve physiological or diagnostic information from the IMD 16. A user may also interact with the programmer 24 to program the IMD 16, e.g., select values for operational parameters of the IMD. For example, a user may interact with the programmer 24 to determine a lower pacing rate limit for a patient based on rate modification information and then configure, or program, the IMD 16 with the lower pacing rate limit.

Further, for example, a user may use the programmer 24 to retrieve information from IMD 16 regarding the rhythm of heart 12, trends therein over time, or tachyarrhythmia episodes. As another example, a user may use the programmer 24 to retrieve information from the IMD 16 regarding other sensed physiological or diagnostic parameters of the patient 14, such as intracardiac or intravascular pressure, activity, posture, respiration, or thoracic impedance. As another example, the user may use the programmer 24 to retrieve information from the IMD 16 regarding the performance or integrity of the IMD 16 or other components of the system 10, such as the leads 18, 20, and 22, or a power source of the IMD 16.

A user may use the programmer 24 to program the lower pacing rate limit, a therapy progression, select electrodes used to deliver defibrillation shocks, select waveforms for the defibrillation shock, or select or configure a fibrillation detection algorithm for the IMD 16. A user may also use the programmer 24 to program aspects of other therapies provided by the IMD 16, such as cardioversion or pacing therapies. In some examples, a user may activate certain features of the IMD 16 by entering a single command via the programmer 24, such as depression of a single key or combination of keys of a keypad or a single point-and-select action with a pointing device.

The IMD 16 and the programmer 24 may communicate via wireless communication using any techniques known in the art. Examples of communication techniques may include, for example, low frequency or radiofrequency (RF) telemetry, but other techniques are also contemplated. In some examples, the programmer 24 may include a programming head that may be placed proximate to the patient's body near the IMD 16 implant site in order to improve the quality or security of communication between the IMD 16 and the programmer 24.

Figure 2:
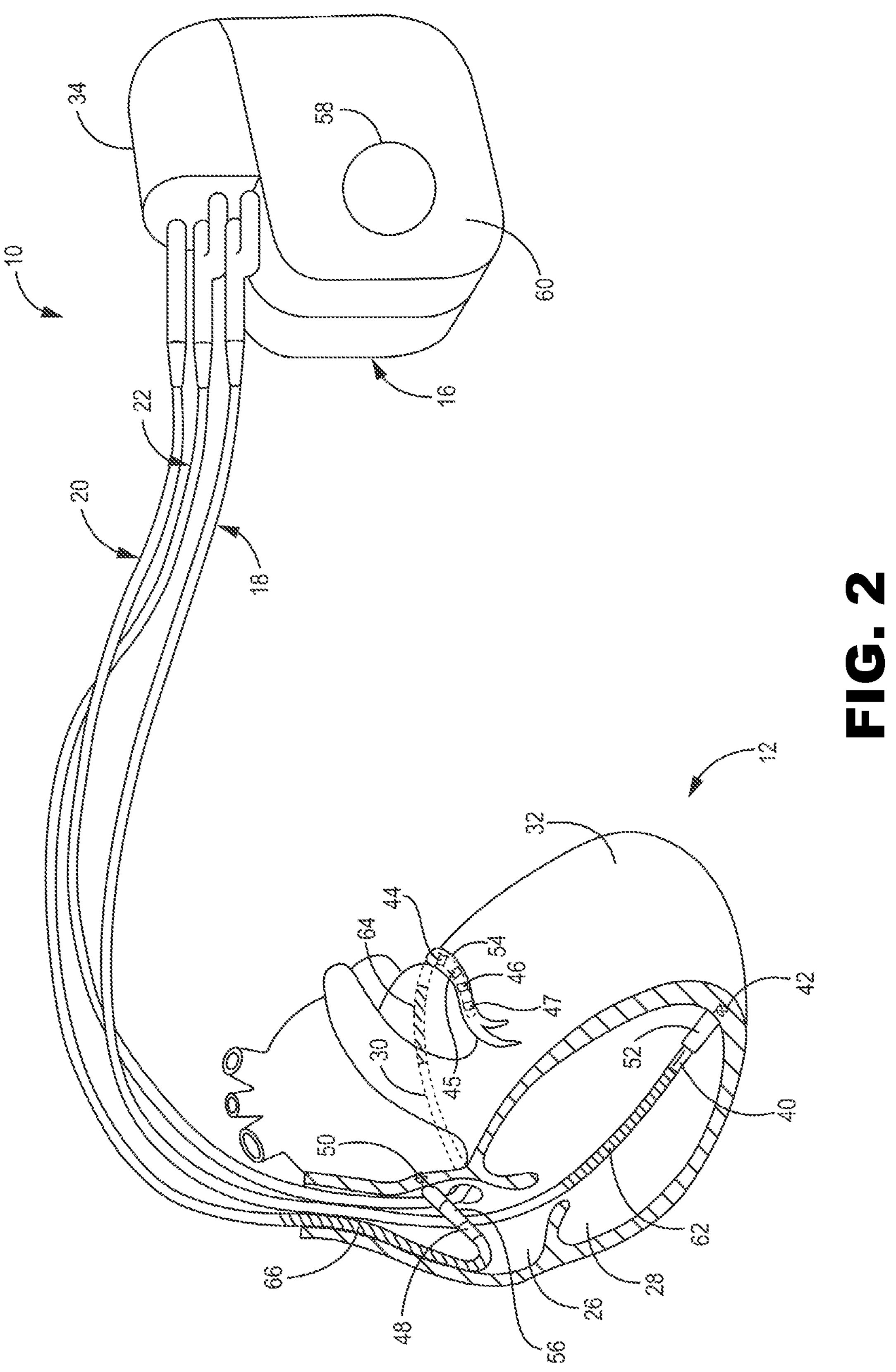
FIG. 2 is a diagram of the illustrative IMD of FIG. 1.

FIG. 2 is a conceptual diagram of the IMD 16 and the leads 18, 20, 22 of therapy system 10 of FIG. 1 in more detail. The leads 18, 20, 22 may be electrically coupled to a therapy delivery module (e.g., for delivery of cardiac remodeling pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of, or define, ring electrodes, and the electrodes 42, 50 may take the form of, or define, extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 2, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The above-described configuration of the therapy system 10 is merely one example. In other examples, the therapy system may include epicardial leads and/or patch electrodes instead of, or in addition to, the transvenous leads 18, 20, 22 illustrated in FIG. 1. In further embodiments, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 1). In one example, the left ventricular (LV) coronary sinus lead 20 extends through one or more veins, the vena cava, the right atrium 26, and into the coronary sinus 30 to a region adjacent to the free wall of the left ventricle 32 of the heart 12. Further, in one or more embodiments, the IMD 16 may not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

Other example therapy systems that provide electrical stimulation therapy to the heart 12 may include any suitable number of leads coupled to the IMD 16, and each of the leads may extend to any location within or proximate to the heart 12. Such other therapy systems may include three transvenous leads located as illustrated in FIGS. 1-2. Still further therapy systems may include a single lead that extends from the IMD 16 into the right atrium 26 or two leads that extend into a respective one of the right atrium 26 and the left atrium. In one example, the IMD 16, as a cardiac resynchronization therapy (CRT) device with a left ventricular (LV) lead may be useful for a HFpEF patient if there is a complete AV node block, as a LV lead can be more beneficial than a RV lead in such patients. In some examples, it can be desirable to deliver rate responsive pacing to the atrium for a HFpEF patient with chronotropic incompetence with an atrial lead (e.g., single chamber atrial system such as AAI) and atrial and ventricular lead system (e.g., dual chamber system such as DDD and VDD).

Figure 3A:
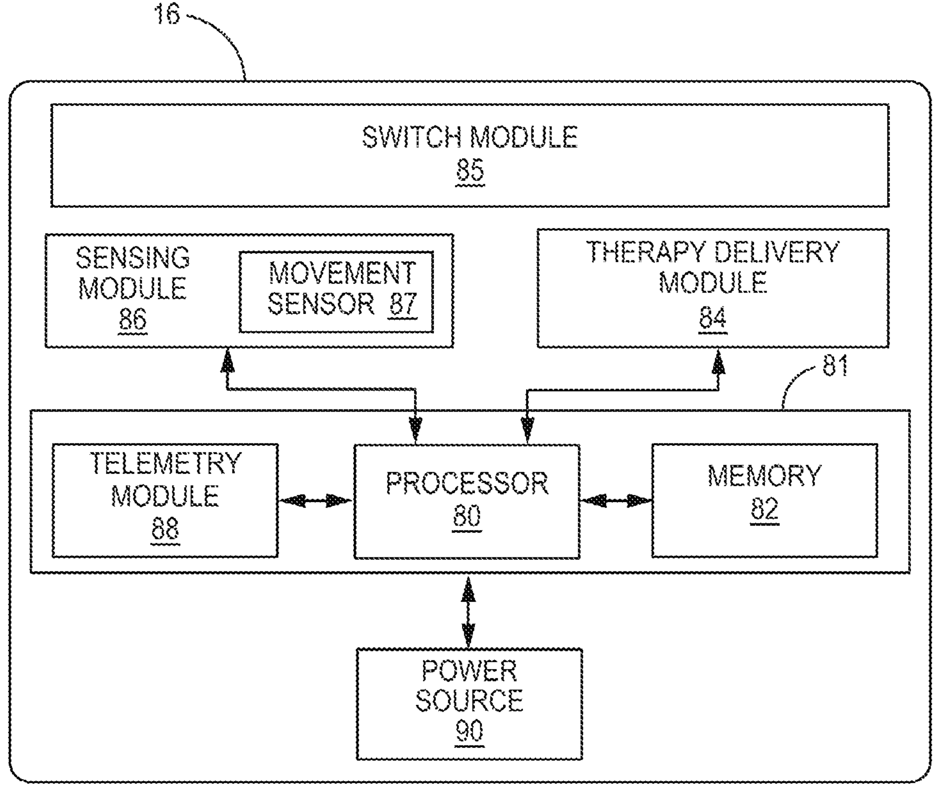
FIG. 3A is a block diagram of the IMD of FIGS. 1-2.

FIG. 3A is a functional block diagram of an illustrative configuration of the IMD 16. As shown, the IMD 16 may include a control module 81, a therapy delivery module 84 (e.g., which may include a stimulation generator), a sensing module 86, and a power source 90. The control module, or apparatus, 81 may include a computing apparatus 80, memory 82, and a telemetry module, or apparatus, 88. The memory 82 may include computer-readable instructions that, when executed, e.g., by the computing apparatus 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically erasable programmable ROM (EEPROM), flash memory, and/or any other digital media.

The computing apparatus 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the computing apparatus 80 may include multiple components, such as any combination of one or more microprocessors, one or more controllers, one or more DSPs, one or more ASICs, and/or one or more FPGAs, as well as other discrete or integrated logic circuitry. The functions attributed to the computing apparatus 80 herein may be embodied as software, firmware, hardware, or any combination thereof.

The control module 81 may control the therapy delivery module, or apparatus, 84 to deliver therapy (e.g., electrical stimulation therapy such as cardiac remodeling pacing) to the heart 12 according to a selected one or more therapy programs, which may be stored in the memory 82, and based on algorithms, or methods, described further below. More, specifically, the control module 81 (e.g., the computing apparatus 80) may control various parameters of the electrical stimulus delivered by the therapy delivery module 84 such as, e.g., A-V delays, pacing pulses with the amplitudes, pulse widths, frequency, or electrode polarities, etc., which may be specified by one or more selected therapy programs (e.g., adaptive pacing therapy program, lower pacing rate limit determination, adjustment, and/or modifications programs, A-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, the therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to the heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module, or apparatus, 85 and the control module 81 (e.g., the computing apparatus 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module, or apparatus, 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus 99, which may include, among additional sensing apparatus, one or more optical sensors to monitor optical signals, one or more mechanical heart activity sensors, as well as the electrodes 40, 42, 44, 45, 46, 47, 48, 50, 58, 62, 64, 66 of FIG. 2. The one or more optical sensors may be used to monitor, among other things, systemic blood pressure, edema, pulse transit time, blood oxygenation (e.g., using pulse oximetry), and presence and concentration of serum biomarkers. The one or more mechanical heart activity sensors may include any suitable transducer components (e.g., mounted within the implanted device, mounted on the can of the device, etc.) for sensing cardiac movements (e.g., valve activity) such as, for example, a sonomicrometer, an accelerometer, or a cardio-mechanical sensor (CMES) employing embedded piezoelectric material. The electrodes may be used to monitor electrical activity of the heart 12, e.g., electrocardiogram (ECG)/electrogram (EGM) signals, and impedance signals. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The sensing apparatus 99 may be physically coupled to the IMD 16 via one or more leads such as shown in FIGS. 1-2 or may be wirelessly coupled to the IMD 16 via telemetry module 88. In one or more embodiments, the sensing apparatus 99 or at least some of the sensing apparatus 99 may be included as another implantable device such as subcutaneous implantable medical device. In other words, multiple implantable devices may interoperate to provide sensing capabilities to provide diagnostics parameters, among other things, as will be described further herein. Additionally, in some embodiment, multiple implantable medical devices may be utilized, each of which may be configured to independently or dependently communicate with other computing devices and external servers as described herein with respect to FIG. 5. One example of sensing apparatus capable of providing pulse transmit times, and in turn, surrogate hemodynamic pressures, among other things, may be found in U.S. Pat. No. 10,182,729 entitled "Systems and Methods for Monitoring Hemodynamic Status" and issued on Jan. 22, 2019, which is incorporated herein by reference in its entirety. Examples of sensing apparatus capable of providing impedance, among other things, may be found in U.S. Pat. No. 9,682,240 entitled "Cardiac Therapy Based Upon Impedance Signals" and issued on Jun. 20, 2017, and U.S. Pat. No. 8,831,721 entitled "Pressure and Impedance Based Discrimination of Hemodynamic Stability" and issued on Sep. 9, 2014, each of which is incorporated herein by reference in its entirety.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any mathematical calculations may be performed by the computing apparatus 80 and any updating of the values or intervals controlled by the pacer timing and control module may be executed, or take place, following such interrupts. A portion of memory 82 may be configured as a plurality of recirculating buffers, capable of holding one or more series of measured intervals, which may be analyzed by, e.g., the computing apparatus 80 in response to the occurrence of a pace or sense interrupt to determine whether the patient's heart 12 is presently exhibiting atrial or ventricular tachyarrhythmia.

Further, the computing apparatus 80 of IMD 16 may detect a tachyarrhythmia episode, such as a ventricular fibrillation, ventricular tachycardia, fast ventricular tachyarrhythmia episode, or a NST episode, based on electrocardiographic activity of heart 12 that is monitored via sensing module 86. For example, sensing module 86, with the aid of at least some of the electrodes 40, 42, 44, 46, 48, 50, 58, 62, 64, and 66 (shown in FIGS. 1-2), may generate an electrocardiogram (ECG) or electrogram (EGM) signal that indicates the electrocardiographic activity. Alternatively, sensing module 86 may be coupled to sense electrodes that are separate from the stimulation electrodes that deliver electrical stimulation to heart 12 (shown in FIGS. 1-2), and may be coupled to one or more different leads than leads 18, 20, 22 (shown in FIGS. 1-2). The ECG signal may be indicative of the depolarization of heart 12.

For example, as previously described, in some examples, computing apparatus 80 (e.g., processor) may identify the presence of a tachyarrhythmia episode by detecting a threshold number of tachyarrhythmia events (e.g., R-R or P-P intervals having a duration less than or equal to a threshold). In some examples, the computing apparatus 80 may also identify the presence of the tachyarrhythmia episode by detecting a variable coupling interval between the R-waves of the heart signal.

The telemetry module 88 of the control module 81 may include any suitable hardware, firmware, software, or any combination thereof for communicating with another device, such as a programmer or mobile computing devices (e.g., a smartphone). For example, under the control of the computing apparatus 80, the telemetry module 88 may receive downlink telemetry from and send uplink telemetry to a programmer or mobile computing device with the aid of an antenna, which may be internal and/or external. The computing apparatus 80 may provide the data to be uplinked to a programmer or a mobile computing device and the control signals for the telemetry circuit within the telemetry module 88, e.g., via an address/data bus. In some examples, the telemetry module 88 may provide received data to the computing apparatus 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
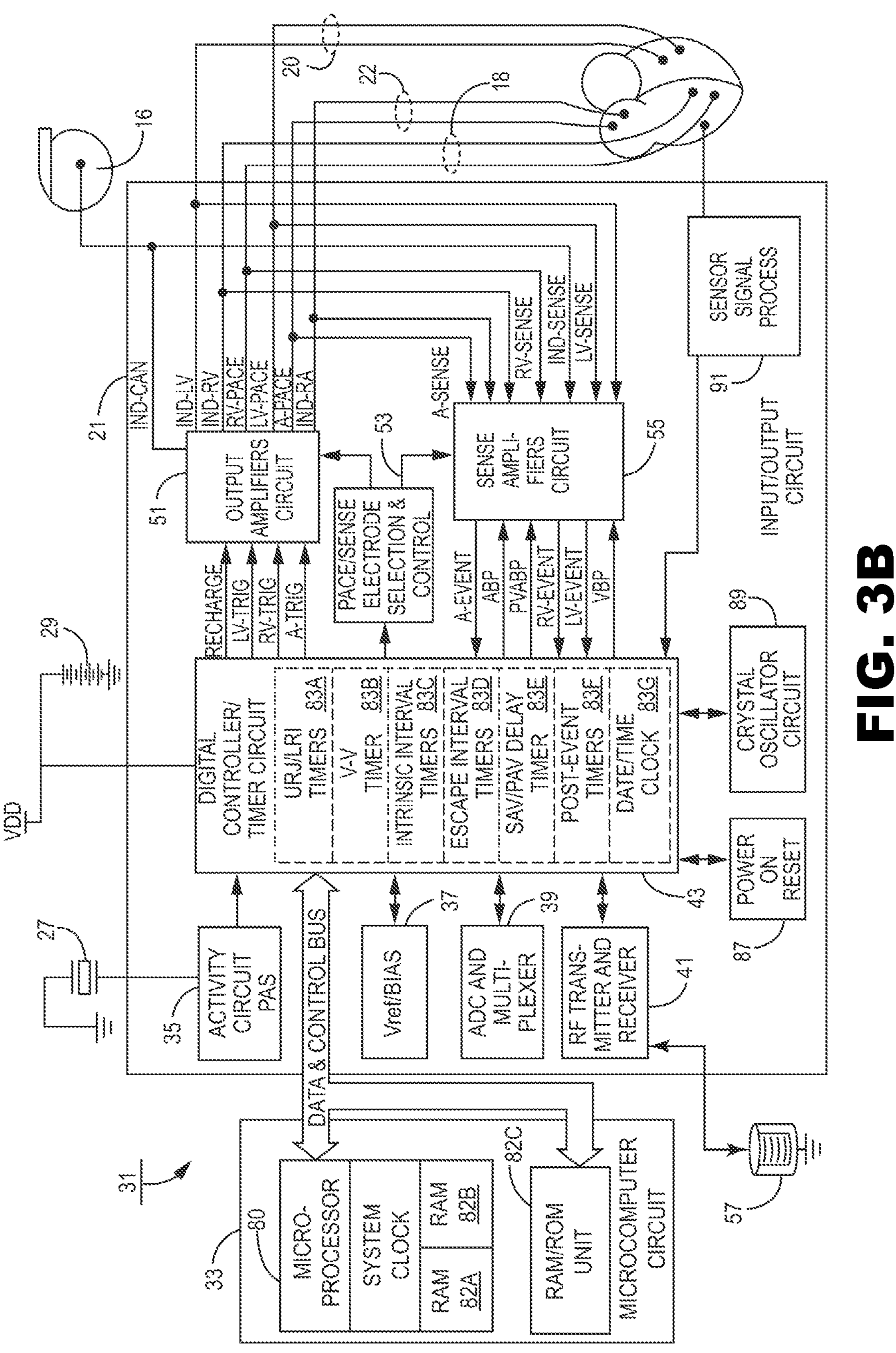
FIG. 3B is another block diagram of IMD circuitry and associated leads employed in the IMD of FIGS. 1-2.

FIG. 3B is a functional block diagram for an embodiment of IMD 16 that depicts bipolar RA lead 22, bipolar RV lead 18 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timer circuit 43 via data and control bus to microcomputer circuitry 33. The IPG circuit 31 is illustrated in a functional block diagram divided generally into the microcomputer circuitry 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers circuit 55 for uplink transmission via RF telemetry transceiver 41. Voltage reference and bias circuit 37, ADC and multiplexer circuit 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the example IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Similarly, the illustrative systems, apparatus, and methods described herein may be practiced in conjunction with alternate types of sensors such as oxygenation sensors, pressure sensors, pH sensors, temperature sensors, respiration sensors, perfusion sensors, heart sound sensors, heart rate sensors, and pulse transit time sensors using one or more various modalities (e.g. optical, sound, electrical, etc.), for use in providing rate responsive pacing capabilities. For example, impedance can be measured using a ring electrode on the lead (e.g., RA or RV lead) and temperature can be measured by a sensor at the distal end of the lead. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF telemetry transceiver 41, which serves both to demodulate received downlink telemetry and to transmit uplink telemetry. Uplink telemetry capabilities may include the ability to transmit stored digital information, e.g., rate modification information such as diagnostic parameters, lower pacing rate limit, activity information, rate responsive pacing information, operating modes and parameters, EGM histograms, and other events, as well as real-time EGMs of atrial and/or ventricular electrical activity and marker channel pulses indicating the occurrence of sensed and paced depolarizations in the atrium and ventricle.

Microcomputer circuitry 33 contains a computing apparatus 80 and associated system clock and on-processor RAM and ROM chips 82A and 82B, respectively. In addition, microcomputer circuitry 33 includes a separate RAM/ROM chip 82C to provide additional memory capacity. Computing apparatus 80 normally operates in a reduced power consumption mode and is interrupt driven. Computing apparatus 80 is awakened in response to defined interrupt events, which may include A-TRIG, RV-TRIG, LV-TRIG signals generated by timers in digital timer circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuitry 33 by way of data and control bus from programmed-in parameter values and operating modes. In addition, if programmed to operate as a rate responsive pacemaker, a timed interrupt, e.g., every cycle or every two seconds, may be provided to allow the microprocessor to analyze the activity sensor data and update the basic pacing rate as well as A-A, V-A, as applicable. In addition, the computing apparatus 80 may also serve to define variable, operative A-V delay intervals, and the energy delivered to each ventricle and/or atrium. Additionally, for example, after each time interrupt, a patient's intrinsic heart rate may be measured and compared to the lower pacing rate limit to determine whether to deliver pacing therapy to maintain the patient's heart rate at or above the lower pacing rate limit.

In one embodiment, computing apparatus 80 is a custom microprocessor adapted to fetch and execute instructions stored in RAM/ROM memory 82 in a conventional manner. It is contemplated, however, that other implementations may be suitable to practice the disclosed methods. For example, an off-the-shelf, commercially available microprocessor or microcontroller, or custom application-specific, hardwired logic, or state-machine type circuit may perform the functions of computing apparatus 80.

Digital controller/timer circuit 43 operates under the general control of the microcomputer circuitry 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals, escape interval timers 83D for timing A-A, and/or V-A pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer circuitry 33. The post-ventricular time periods include a post-ventricular atrial blanking period (PVARP), a post-atrial ventricular blanking period (PAVBP), a ventricular blanking period (VBP), and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The computing apparatus 80 also optionally calculates A-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. To trigger generation of an RV-PACE or LV-PACE pulse, digital controller/timer circuit 43 may utilize the algorithms described below.

The output amplifiers circuit 51 includes switching circuits for coupling selected pace electrode pairs from among the lead conductors and the IND-CAN electrode to the RA pace pulse generator (and LA pace pulse generator if provided), RV pace pulse generator and LV pace pulse generator. Pace/sense electrode selection and control circuit 53 selects lead conductors and associated pace electrode pairs to be coupled with the atrial and ventricular output amplifiers within output amplifiers circuit 51 for accomplishing RA, LA, RV, and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers circuit 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

Figure 4:
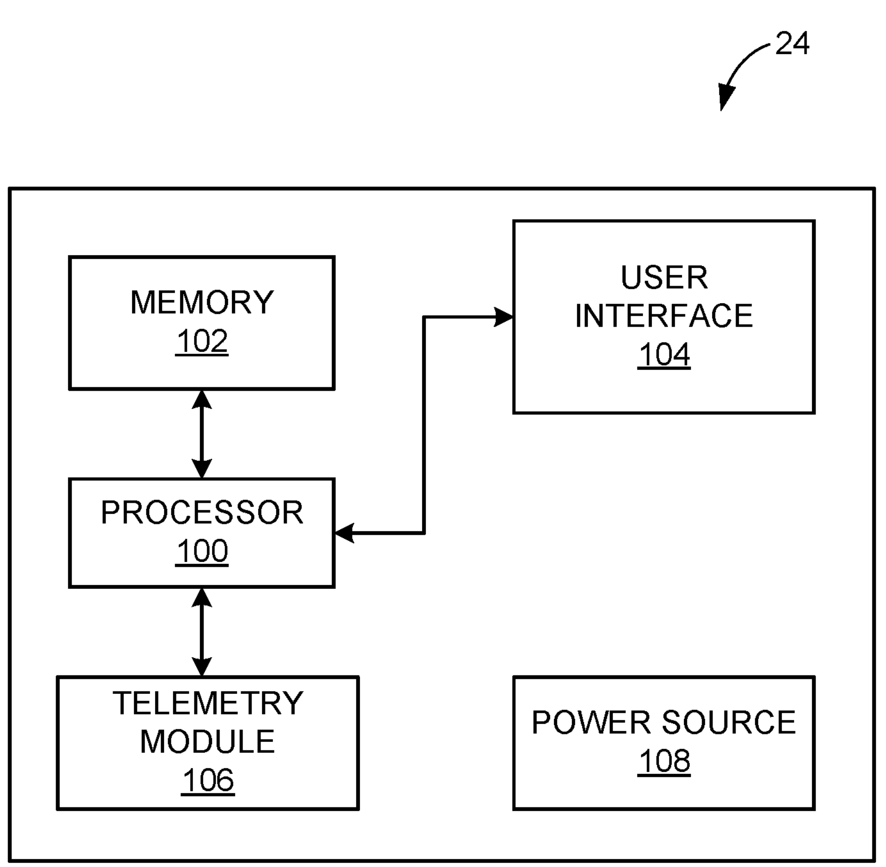
FIG. 4 is a diagram of an illustrative programmer of the system of FIG. 1.

FIG. 4 is block diagram of an illustrative programmer 24. As shown in FIG. 4, the programmer 24 includes a processor

100, a memory 102, a user interface 104, a telemetry module 106, and a power source 108. The programmer 24 may be a dedicated hardware device with dedicated software for programming of IMD 16. Alternatively, the programmer 24 may be an off-the-shelf computing device (e.g., mobile compute device such as a smartphone) running an application that enables programmer 24 to program IMD 16.

A user may use the programmer 24 to select therapy programs (e.g., sets of stimulation parameters), generate new therapy programs, modify therapy programs through individual or global adjustments or transmit the new programs to a medical device, such as the IMD 16 (FIG. 1). The clinician may interact with the programmer 24 via the user interface 104, which may include display to present graphical user interface to a user, and a keypad or another mechanism for receiving input from a user.

The processor 100 can take the form one or more microprocessors, DSPs, ASICs, FPGAs, programmable logic circuitry, or the like, and the functions attributed to processor 100 herein may be embodied as hardware, firmware, software or any combination thereof. The memory 102 may store instructions that cause processor 100 to provide the functionality ascribed to the programmer 24 herein, and information used by processor 100 to provide the functionality ascribed to the programmer 24 herein. The memory 102 may include any fixed or removable magnetic, optical, or electrical media, such as RAM, ROM, CD-ROM, hard or floppy magnetic disks, EEPROM, or the like. The memory 102 may also include a removable memory portion that may be used to provide memory updates or increases in memory capacities. A removable memory may also allow IMD and/or patient data to be easily transferred to another computing device, or to be removed before the programmer 24 is used to program therapy for another patient. The memory 102 may also store information that controls therapy delivery by the IMD 16, such as stimulation parameter values.

The programmer 24 may communicate wirelessly with the IMD 16, such as using RF communication or proximal inductive interaction. This wireless communication is possible through the use of the telemetry module 106, which may be coupled to an internal antenna or an external antenna. An external antenna that is coupled to programmer 24 may correspond to the programming head that may be placed over the heart 12, as described above with reference to FIG. 1. The telemetry module 106 may be similar to telemetry module 88 of the IMD 16 (FIG. 3A).

The telemetry module 106 may also be configured to communicate with another computing device via wireless communication techniques, or direct communication through a wired connection. Examples of local wireless communication techniques that may be employed to facilitate communication between the programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with the programmer 24 without needing to establish a secure wireless connection.

The power source 108 delivers operating power to the components of programmer 24. The power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium-ion batteries) may be used. In addition, programmer 24 may be directly coupled to an alternating current outlet to power the programmer 24. The power source 108 may include circuitry to monitor power remaining within a battery. In this manner, a user interface 104 may provide a current battery level indicator or low battery level indicator when the battery needs to be replaced or recharged. In some cases, power source 108 may be capable of estimating the remaining time of operation using the current battery.

Figure 5:
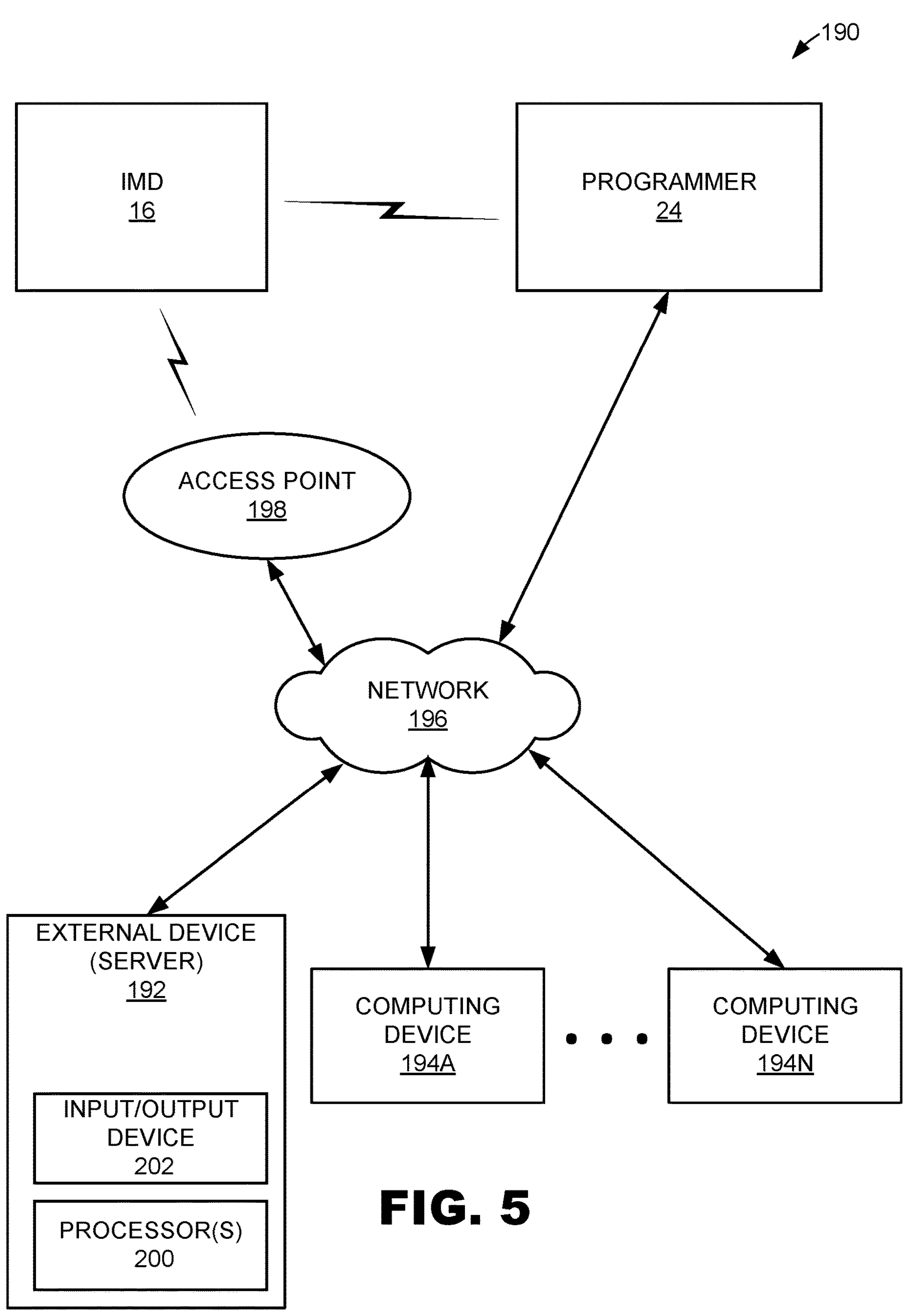
FIG. 5 is a diagram of an illustrative system including the IMD and programmer of FIG. 1 and additional devices coupled thereto via a network.

FIG. 5 is a block diagram illustrating a system 190 that includes an external device 192, such as a server, and one or more computing devices 194A-194N that are coupled to the IMD 16 and the programmer 24 shown in FIGS. 1-4 via a network 196, according to one embodiment. In this embodiment, the IMD 16 may use its telemetry module 88 to communicate with the programmer 24 via a first wireless connection, and to communicate with an access point 198 via a second wireless connection. In the example of FIG. 5, the access point 198, the programmer 24, the external device 192, and the computing devices 194A-194N are interconnected, and able to communicate with each other, through a network 196. In some cases, one or more of the access point 198, the programmer 24, the external device 192, and the computing devices 194A-194N may be coupled to the network 196 through one or more wireless connections. The IMD 16, the programmer 24, the external device 192, and the computing devices 194A-194N may each include, or comprise, one or more processors, such as one or more microprocessors, DSPs, ASICs, FPGAs, programmable logic circuitry, or the like, that may perform various functions and operations, such as those described herein.

The access point 198 may include, or comprise, a device that connects to the network 196 via any of a variety of connections, such as cellular data connection, telephone dial-up, digital subscriber line (DSL), or cable modem connections. In other examples, the access point 198 may be coupled to the network 196 through different forms of connections, including wired or wireless connections. In some examples, the access point 198 may communicate with the programmer 24 and/or the IMD 16. The access point 198 may be co-located with the patient 14 (e.g., within the same room or within the same site as the patient 14) or may be remotely located from the patient 14. For example, the access point 198 may be a home monitor that is located in the patient's home or is portable for carrying with the patient 14.

During operation, the IMD 16 may collect, measure, and store various forms of diagnostic data such as, e.g., diagnostic parameters that may be utilized by the illustrative systems, methods, and processes to determine, or generate, a lower pacing rate limit. In certain cases, the IMD 16 may directly analyze collected diagnostic data and generate any corresponding reports or alerts. In some cases, however, the IMD 16 may send diagnostic data such as the diagnostic parameters, to the programmer 24, the access point 198, and/or the external device 192, either wirelessly or via the access point 198 and the network 196, for remote processing and analysis (e.g., to determine a lower pacing rate limit).

In another example, the IMD 16 may provide the external device 192 with collected diagnostic data or parameters via the access point 198 and the network 196. The external device 192 includes one or more the processors 200. In some cases, the external device 192 may request such data, and in some cases, the IMD 16 may automatically or periodically provide such data to the external device 192. Upon receipt of the diagnostic data via the input/output device 202, the external device 192 may be capable of analyzing the data and generating reports, alerts, or other values (e.g., a lower pacing rate limit).

One or more of the computing devices 194A-194N may access the diagnostic data or parameters through the network 196 for use in determining, or generating, a lower pacing rate limit. In some cases, the external device 192 may automatically send the generated lower pacing rate limit to via the input/output device 202 to one or more of the computing devices 194A-194N. In some cases, the external device 192 may send the lower pacing rate limit to another device, such as the programmer 24, either automatically or upon request. In some cases, the external device 192 may display the lower pacing rate limit to a user via the input/output device 202.

In one embodiment, the external device 192 may comprise a secure storage site for diagnostic data or information that has been collected from the IMD 16 and/or the programmer 24. In this embodiment, the network 196 may comprise an Internet network, and trained professionals, such as clinicians, may use the computing devices 194A-194N to securely access stored diagnostic data or parameters or lower pacing rate limits on the external device 192. For example, the trained professionals may utilize secure usernames and passwords to access the stored information on the external device 192. In one embodiment, the external device 192 may be a CareLink server provided by Medtronic, Inc., of Minneapolis, Minnesota.

Figure 6:
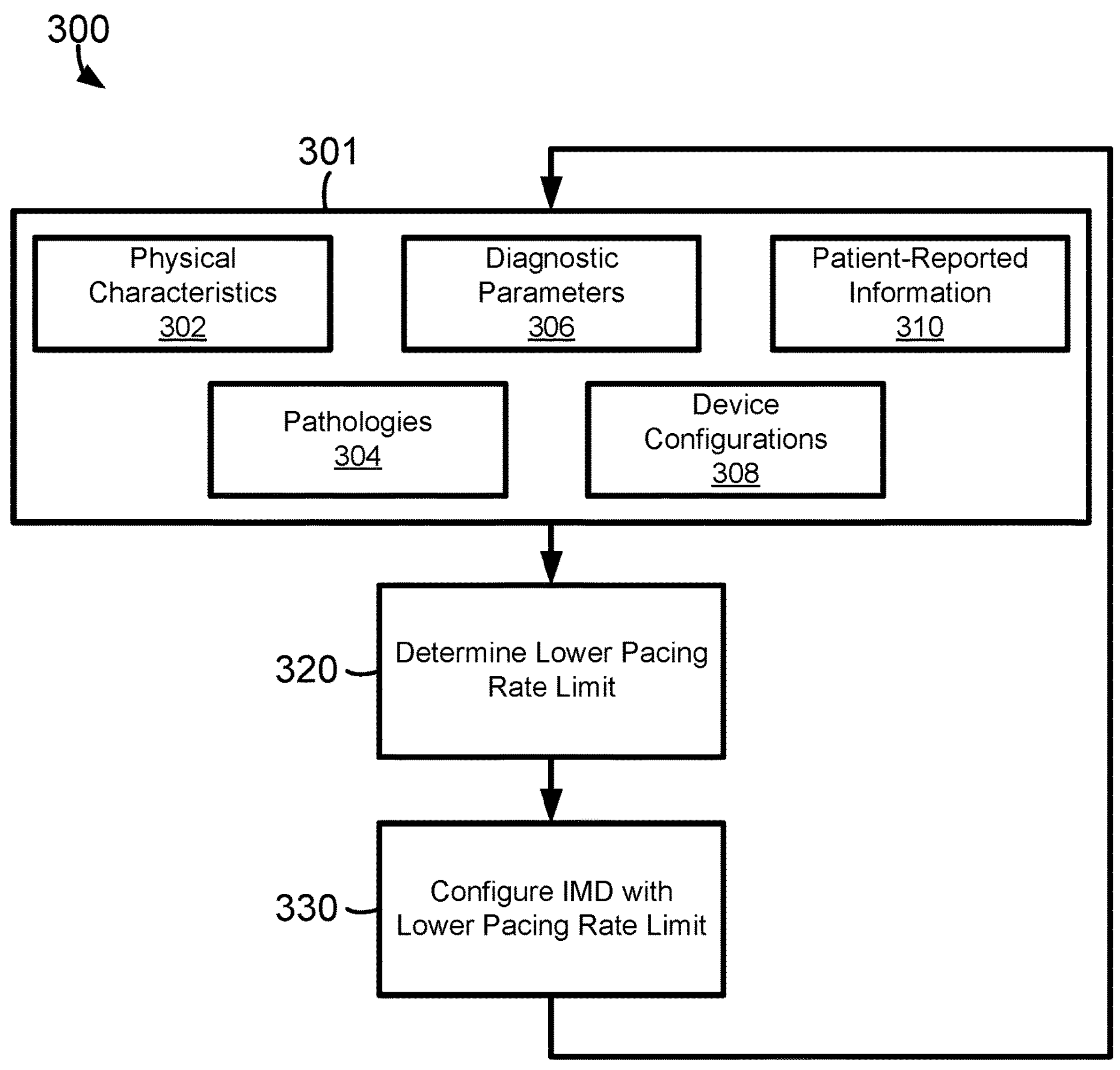
FIG. 6 is an illustrative method of determining of lower pacing rate limit, e.g., using the system and devices of FIGS. 1-5.
Figure 7:
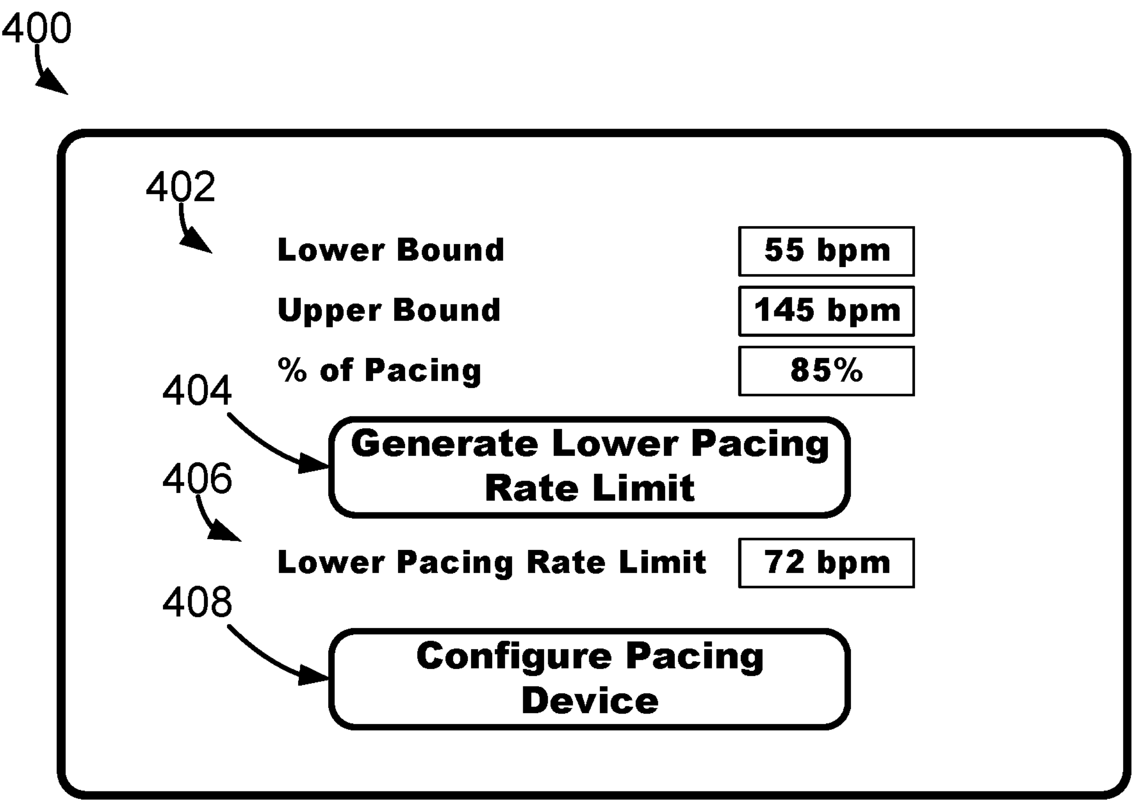
FIG. 7 is an illustrative graphical user interface for use in determining a lower pacing rate limit, e.g., using the system, devices, and methods of FIGS. 1-6.

An illustrative method 300 of determining of lower pacing rate limit, e.g., using the system and devices of FIGS. 1-5, is depicted in FIG. 6. The illustrative method 300 utilizes rate modification information of a specific patient to determine the lower pacing rate limit for pacing device of the specific patient. In other words, illustrative method 300 may tailor a lower pacing rate limit for a specific patient and the specific conditions of the patient. It is be understood that, during adaptive pacing therapy, the lower pacing rate limit may change based on one or more factors such as activity level, and thus, determined lower pacing rate limit described herein is the baseline lower pacing rate limit, which may be increased during adaptive pacing therapy.

Before determining the lower pacing rate limit, the method 300 first obtains rate modification information 301. The rate modification information may be described as any information specific to the patient that may correlate to lower pacing rate limit so as to be able to be used to determine lower pacing rate limit (e.g., an optimized lower pacing rate limit) for a patient. The rate modification information may be categorized into one or more of a plurality of different categories. For example and as shown, the rate modification information may include physical characteristics 302 of the patient, pathologies 304 of the patient, diagnostic parameters 306 of the patient, device configurations 308 of the pacing device, and patient-reported information 310, each of which will be described further herein.

The physical characteristics 302 may include, among other things, height, sex, age, body mass index (BMI), body surface area, physical fitness level, and activity level. The pathologies 304 may include, among other things, diastolic dysfunction/heart failure with preserved ejection fraction, systolic dysfunction, chronotropic incompetence, worsening heart failure, and comorbid disease. The diagnostic parameters 306 may include, among other things, ventricular contractility, ventricular stiffness, pulse transit time, resting heart rate, nighttime heart rate, arrhythmia burden, targeted pacing burden, heart rate recovery, impedance, fluid overload, edema, respiration rate, maximum heart rate, ejection fraction, left ventricular pressure, systemic blood pressure, pulmonary artery pressure, blood oxygenation, and presence or concentration of serum biomarkers. The device configurations 308 may include, among other things, ventricular pacing electrode location, atrial pacing electrode location, and type of pacing therapy. The patient-reported information 310 may include, among other things, energy level, peripheral edema, desired activity performance, and pacing-related symptoms.

It is to be understood that, although five different categories of rate modification information as described herein and shown in FIG. 6, more than five and less than five different categories of rate modification information are contemplated by the present disclosure. Further, although different categories of rate modification information, each including a plurality of different data or informational items, less than all of the different data items (e.g., such as one data item, two data items, three data items, etc.) across the five categories may be obtained and later utilized by the illustrative method 300. For example, a single data, or information, item such as age may be obtained 301, and then later utilized to determine a lower pacing rate limit for a patient. Further, for example, a single data, or information, item such as the pathology of diastolic dysfunction/heart failure with preserved ejection fraction may be obtained 301, and then later utilized to determine a lower pacing rate limit for a patient. Still further, for example, two data, or information, items such as the patient-reported desired activity performance and the diagnostic parameter of nighttime heart rate may be obtained 301, and then later utilized to determine a lower pacing rate limit for a patient.

Furthermore, the rate modification information may be obtained from one or more of plurality of different sources such as, for example, computer systems and medical devices such as a pacing device implanted in the patient, an external ECG monitoring system, other implanted medical devices, watches, etc. For instance, a user such as a clinician may enter, or input, the rate modification information into a computer system that is configured to obtain the rate modification information. More specifically, for example, a nurse may measure and then enter the physical characteristics of the patient into a computer system such as the programmer 24, the computing devices 194*n*, and external device 192 described herein. Additionally, the rate modification information may be obtained via a network 196 described herein from an electronic medical records system, e.g., located on an external device 192. Furthermore, the pacing device implanted in the patient and/or another medical device associated with and monitoring the patient may obtain various rate modification information such as pathologies 304, diagnostic parameters 306, and/or device configurations 308. More specifically, for example, an IMD implanted in a patient may be able to report the type of therapy being provided to the patient, the patient's heart rate, the patient's resting heart rate, etc. to one or more additional systems such as the programmer 24, the computing devices 194*n*, and external device 192 described herein. Additionally, the patient-reported information 310 may be obtained 301 by the patient inputting, or entering, such information into a mobile computing device. In one or more embodiment, a mobile computing device may ask a patient a series of questions the answers of which may include rate modification information.

Upon obtaining at least one piece, or item, of rate modification information 301, the illustrative method 300 may then determine the lower pacing rate limit based on the at least one piece, or item, of rate modification information 320. In other words, the rate modification information may be utilized to calculate, or generate, the lower pacing rate limit for the patient. It is to be understood that the determination 320 may be executed, or occur, on a variety of different devices or systems such as the IMD 16, the programmer 24, the computing devices 194*n*, and external device 192.

The determination of the lower pacing rate limit 320 may utilize a defined relationship, or function, between the at least one piece, or item, of rate modification information and the lower pacing rate limit generated from, e.g., clinical data. For example, as height decreases, the lower pacing rate limit may be higher than a default lower pacing rate limit (e.g., a default lower pacing rate limit may be about 60 beats per minute). Further, for example, if the patient is a female, the lower pacing rate limit may be higher than a default lower pacing rate limit, and if the patient is a male, the lower pacing rate limit may be lower than a default lower pacing rate limit. Further, for example, the younger the age of the patient, the lower pacing rate limit may be higher than a default lower pacing rate limit. Still further, for example, as body mass index increases, the lower pacing rate limit may be higher than a default lower pacing rate limit. And still further, for example, as body surface area decreases, the lower pacing rate limit may be higher than a default lower pacing rate limit. Yet still further, as physical fitness of the patient decreases, the lower pacing rate limit may be higher than a default lower pacing rate limit. Lastly, as activity level of the patient increases, the lower pacing rate limit may be higher than a default lower pacing rate limit.

With respect to diagnostic parameters, for example, as ventricular stiffness increases, the lower pacing rate limit may be higher than a default lower pacing rate limit. Further, for example, as pulse transit time decreases, the lower pacing rate limit may be higher than a default lower pacing rate limit. Further, for example, as resting heart rate and/or nighttime heart rate increases, the lower pacing rate limit may be higher than a default lower pacing rate limit. Still further, for example, the lower pacing rate limit may be increased to greater than a default lower pacing rate limit to increase pacing burden. Still further, for example, as ejection fraction increases, the lower pacing rate limit may be higher than a default lower pacing rate limit. Still further, for example, as edema increases, the lower pacing rate limit may be increased to be higher than a default lower pacing rate limit, and conversely, as edema decreases, the lower pacing rate limit may be decreased to be lower than the default lower pacing rate limit. Still further, for example, as blood pressure increases, the lower pacing rate limit may be increased to be higher than a default lower pacing rate limit. Yet still further, for example, as pulmonary artery pressure increases, the lower pacing rate limit may be increased to be higher than a default lower pacing rate limit. And still further, for example, with respect to a biomarker such as NT-proBNP, as NT-proBNP increases, the lower pacing rate limit may be increased to be higher than a default lower pacing rate limit.

Furthermore, with respect to pathologies, for example, if a patient has diastolic dysfunction, then the lower pacing rate limit may be higher than a default lower pacing rate limit. Further, for example, if a patient has systolic dysfunction, then the lower pacing rate limit may be lower than a default lower pacing rate limit to, e.g., minimize pacing percentage. Still further, for example, if a patient has chronotropic incompetence, then the lower pacing rate limit may be higher than a default lower pacing rate limit (to, e.g., compensate for insufficient heart rate during exercise). Additionally, if a patient has the pathology of heart failure with preserved ejection fraction (HFpEF), the lower pacing rate limit may be determined to be higher than a default lower pacing rate limit. Further, if a patient has the pathology of heart failure with reduced ejection fraction (HFrEF), the lower pacing rate limit may be determined to be lower than a default lower pacing rate limit.

Additionally, with respect to device characteristics, for example, if cardiac conduction system pacing is the type of pacing therapy being delivered (e.g., the pacing electrode is positioned to pace the cardiac conduction system), then the lower pacing rate limit may be higher than a default lower pacing rate limit. Further, for example, if the pacing device is configured to deliver cardiac resynchronization therapy pacing, then the lower pacing rate limit may be higher than a default lower pacing rate limit.

When using patient-reported information, the processes may be designed to determine lower pacing rate limit to minimize undesirable symptoms or conditions and/or meet patient expectations such as, e.g., a desired performance level. For example, if a patient reports one or more undesirable symptoms, then the lower pacing rate limit may be lower than a default lower pacing rate limit or reduced from its present value. Further, for example, if a patient provides patient-reported information that the patient would like an increased physical performance level, then the lower pacing rate limit may be incrementally increased over a period of time until the patient reports undesired symptoms. In this way, the lower pacing rate limit may be "titrated" by the patient to find the optimal lower pacing rate limit for the patient at present state. For example, if a patient reports a low energy level, then the lower pacing rate limit may be higher than a default lower pacing rate limit.

Additionally, it is be understood that having an increased lower pacing rate limit (e.g., higher than a default lower pacing rate limit), may result in undesirable effect since, for example, a pacing device may pace a higher percentage of the time, which may be undesirable when utilizing traditional pacing locations (e.g., RV apex). Nonetheless, pacing a higher percentage of the time may not achieve the same undesired effects when utilizing cardiac conduction system pacing. As such, if the type of pacing is traditional myocardial tissue pacing, it may be determined to not increase the lower pacing rate limit beyond the default lower pacing rate limit, and if the type of pacing is cardiac conduction system pacing, it may be determined to increase the lower pacing rate limit beyond the default lower pacing rate limit.

Upon determination of the lower pacing rate limit 320, the pacing device may be configured, or programmed, with the lower pacing rate limit 330. In one or more embodiments, the determined lower pacing rate limit may be presented, or shown, to a clinician for their review, potential adjustment, and approval prior to configuring the pacing device of the patient. In embodiments where the lower pacing rate limit determination occurs in the pacing device itself, the pacing device itself may re-configure itself with the newly determined lower pacing rate limit. In other words, determining the lower pacing rate limit is performed, or executed, by the pacing device, such as IMD 16, may. Additionally, in one or more embodiments, the lower pacing rate limit may be determined using one or more of the computing devices 194*n* and external device 192 described herein, and then may be transmitted to the pacing device via the network 196 and/or the programmer 24. In other words, a remote computing device may perform, or execute, the determination of the lower pacing rate limit.

Additionally, it is to be understood that the method 300 may be performed cyclically, or iteratively, over a period of time, such as, e.g., every day, every week, once a month, every three months, etc. In this way, the lower pacing rate limit of the pacing device may be updated to correspond with changing conditions of the patient, updated clinical data indicating how rate modification information relates, or corresponds, to lower pacing rate limit, etc. For example, the pacing device may monitor, or obtain, left ventricular ejection fraction, and then determine the lower pacing rate limit based on left ventricular ejection fraction, periodically.

An illustrative graphical user interface 400 for use in determining a lower pacing rate limit, e.g., using the system, devices, and methods of FIGS. 1-6. The graphical user interface 400 may be utilized by a clinician to determine a lower pacing rate limit for a patient at implantation or during a follow-up consultation. The graphical user interface 400 includes an input region 402 configured for the clinician to input, or enter, a few optional preferences. In particular, the input region 402 includes a lower bound input area, an upper bound input area, and a percentage of pacing desired input area, each of which may be selected (e.g., touched, clicked, etc.) by a clinician to enter a value therein. The lower bound input area may allow a clinician to enter a lower boundary, or limit, for pacing to be delivered to the patient, and the upper bound input area may allow a clinician to enter an upper boundary, or limit, for pacing to be delivered to the patient. The percentage of pacing desired input area may allow a clinician to enter a desired % of time that the patient is to optimally receive pacing therapy. The illustrative methods and processes for determining the lower pacing rate limit 320 may take into consideration each of the lower boundary, upper boundary, and % of desired pacing when determining, or generating, the lower pacing rate limit. For example, the determined lower pacing rate limit would not exceed the upper bound or be less than the lower bound and may be determined such that the % of desired pacing time is likely not exceeded.

After optionally entering the values into the input region 402, the clinician may select the generate lower pacing rate limit region 404 that may utilize method 300 described herein in conjunction with the values entered into the input region 402 to generate a lower pacing rate limit, which is displayed in the lower pacing rate limit display region 406. Afterwards and upon review, the clinician may select the configure pacing device region 408 to configure the pacing device with the generated lower pacing rate limit.

EXAMPLES

Example Ex1: A method comprising:

- obtaining rate modification information comprising at least one physical characteristic of a patient utilizing a pacing device; and
- determining a lower pacing rate limit for the pacing device based on the obtained rate modification information, wherein the lower pacing rate limit is utilized by the pacing device to initiate pacing in response to the patient's intrinsic rate being less than the lower pacing rate limit.

Example Ex2: A system comprising:

- a computing apparatus comprising one or more processors and configured to:
  - obtain rate modification information comprising at least one physical characteristic of a patient utilizing a pacing device; and
  - determine a lower pacing rate limit for the pacing device based on the obtained rate modification information, wherein the lower pacing rate limit is utilized by the pacing device to initiate pacing in response to the patient's intrinsic rate being less than the lower pacing rate limit.

Example Ex3: An implantable medical device comprising:

- one or more electrodes to deliver cardiac pacing therapy to and sense electrical activity from a patient's heart; and
- a computing apparatus operably coupled the one or more electrodes and comprising one or more processors, the computing apparatus configured to:
  - monitor the patient's intrinsic heart rate using the one or more electrodes;
  - deliver pacing therapy to the patient's heart in response to the patient's intrinsic rate being less than a lower pacing rate limit;
  - obtain rate modification information comprising at least one physical characteristic of a patient utilizing a pacing device; and
  - determine a lower pacing rate limit for the pacing device based on the obtained rate modification information.

Example Ex4: The method as in Example Ex1, the system as in Example Ex2, or the device as in Example Ex3, wherein the at least one physical characteristic comprises one or more of height, sex, age, body mass index (BMI), body surface area, physical fitness level, and activity level.

Example Ex5: The method, system, or device as any one of Examples Ex1-Ex4, wherein the rate modification information further comprises at least one pathology, wherein the at least one pathology comprises diastolic dysfunction/heart failure with preserved ejection fraction.

Example Ex6: The method, system, or device as any one of Examples Ex1-Ex5, wherein the rate modification information further comprises at least one pathology, wherein the at least one pathology comprises one or more of systolic dysfunction, chronotropic incompetence, worsening heart failure, and comorbid disease.

Example Ex7: The method, system, or device as any one of Examples Ex1-Ex6, wherein the rate modification information further comprises at least one diagnostic parameter, wherein the at least one diagnostic parameter comprises one or more ventricular contractility, ventricular stiffness, pulse transit time, resting heart rate, nighttime heart rate, arrhythmia burden, targeted pacing burden, heart rate recovery, impedance, fluid overload, edema, respiration rate, maximum heart rate, ejection fraction, left ventricular pressure, systemic blood pressure, pulmonary artery pressure, blood oxygenation, and presence or concentration of serum biomarkers.

Example Ex8: The method, system, or device as Examples Ex7, wherein obtaining rate modification information comprising monitoring the at least one diagnostic parameter of the patient using the pacing device.

Example Ex9: The method, system, or device as any one of Examples Ex1-Ex8, wherein the rate modification information further comprises at least one device configuration, wherein the at least one device configuration comprises one or more of ventricular pacing electrode location, atrial pacing electrode location, and type of pacing therapy.

Example Ex10: The method, system, or device as any one of Examples Ex1-Ex9, wherein the rate modification information further comprises patient-reported information, wherein the patient-reported information comprises one or more of energy level, peripheral edema, desired activity performance, and pacing-related symptoms.

Example Ex11: The method, system, or device as any one of Examples Ex1-Ex10, wherein the rate modification information further comprises patient-reported information, wherein the patient-reported information is obtained from a mobile computing device.

Example Ex12: The method or system as any one of Examples Ex1-Ex2 and Ex4-Ex11, wherein the method further comprises or the computing apparatus is further configured to execute configuring the pacing device with the lower pacing rate limit.

Example Ex13: The method, system, or device as any one of Examples Ex1-Ex12, wherein obtaining rate modification information comprising obtaining the rate modification information from an electronic medical records system.

Example Ex14: The method as any one of Examples Ex1 and Ex4-Ex10, wherein determining a lower pacing rate limit for the pacing device based on the obtained rate modification information is performed by the pacing device.

Example Ex15: The method or system as any one of Examples Ex1-Ex2 and Ex4-Ex14, wherein determining a lower pacing rate limit for the pacing device based on the obtained rate modification information is performed by a remote computing system communicatively coupled to the pacing device.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described methods, processes, and techniques, including those attributed to the IMD 16, the programmer 24, the external device 192, and computing devices 194N, may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. The terms "computing apparatus," "controller" "module," "processor," or "processing circuitry" may generally refer to any of the foregoing logic circuitry, alone or in combination with other logic circuitry, or any other equivalent circuitry. Also, the techniques could be fully implemented in one or more circuits or logic elements. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

What is claimed:

1. A method comprising:

obtaining rate modification information comprising at least one physical characteristic of a patient utilizing a pacing device and at least one diagnostic parameter, the at least one diagnostic parameter comprising a night-time heart rate;

receiving an upper bound, a lower bound, and a percentage of pacing threshold; and determining a lower pacing rate limit for the pacing device based on the obtained rate modification information, the upper bound, the lower bound, and the percentage of pacing threshold, wherein the lower pacing rate limit is increased when a percentage of paced beats exceeds the percentage of pacing threshold and wherein the lower pacing rate limit is utilized by the pacing device to initiate pacing in response to the patient's intrinsic rate being less than the lower pacing rate limit.

2. The method of claim 1, wherein the at least one physical characteristic comprises one or more of height, sex, age, body mass index (BMI), body surface area, physical fitness level, and activity level.

3. The method of claim 1, wherein the rate modification information further comprises at least one pathology, wherein the at least one pathology comprises diastolic dysfunction/heart failure with preserved ejection fraction.

4. The method of claim 1, wherein the rate modification information further comprises at least one pathology, wherein the at least one pathology comprises one or more of systolic dysfunction, chronotropic incompetence, worsening heart failure, and comorbid disease.

5. The method of claim 1, wherein the at least one diagnostic parameter further comprises one or more of ventricular contractility, ventricular stiffness, pulse transit time, resting heart rate, arrhythmia burden, targeted pacing burden, heart rate recovery, impedance, fluid overload, edema, respiration rate, maximum heart rate, ejection fraction, left ventricular pressure, systemic blood pressure, pulmonary artery pressure, blood oxygenation, and presence or concentration of serum biomarkers.

6. The method of claim 5, wherein obtaining rate modification information comprising monitoring the at least one diagnostic parameter of the patient using the pacing device.

7. The method of claim 1, wherein the rate modification information further comprises at least one device configuration, wherein the at least one device configuration comprises one or more of ventricular pacing electrode location, atrial pacing electrode location, and type of pacing therapy.

8. The method of claim 1, wherein the rate modification information further comprises patient-reported information, wherein the patient-reported information comprises one or more of energy level, peripheral edema, desired activity performance, and pacing-related symptoms.

9. The method of claim 1, wherein the rate modification information further comprises patient-reported information, wherein the patient-reported information is obtained from a mobile computing device.

10. The method of claim 1, wherein the method further comprises configuring the pacing device with the lower pacing rate limit.

11. The method of claim 1, wherein obtaining rate modification information comprising obtaining the rate modification information from an electronic medical records system.

12. The method of claim 1, wherein determining a lower pacing rate limit for the pacing device based on the obtained rate modification information is performed by the pacing device.

13. The method of claim 1, wherein determining a lower pacing rate limit for the pacing device based on the obtained rate modification information is performed by a remote computing system communicatively coupled to the pacing device.

14. A system comprising:

a computing apparatus comprising one or more processors and configured to:

obtain rate modification information comprising at least one physical characteristic of a patient utilizing a pacing device and at least one diagnostic parameter, the at least one diagnostic parameter comprising a nighttime heart rate;

receive an upper bound, a lower bound, and a percentage of pacing threshold; and determine a lower pacing rate limit for the pacing device based on the obtained rate modification information, the upper bound, the lower bound, and the percentage of pacing threshold, wherein the lower pacing rate limit is increased when a percentage of paced beats exceeds the percentage of pacing threshold and wherein the lower pacing rate limit is utilized by the pacing device to initiate pacing in response to the patient's intrinsic rate being less than the lower pacing rate limit.

15. The system of claim 14, wherein the at least one physical characteristic comprises one or more of height, sex, age, body mass index (BMI), body surface area, physical fitness level, and activity level.

16. The system of claim 14, wherein the rate modification information further comprises at least one pathology, wherein the at least one pathology comprises diastolic dysfunction/heart failure with preserved ejection fraction.

17. The system of claim 14, wherein the rate modification information further comprises at least one pathology, wherein the at least one pathology comprises one or more of systolic dysfunction, chronotropic incompetence, worsening heart failure, and comorbid disease.

18. The system of claim 14, wherein the at least one diagnostic parameter further comprises one or more of ventricular contractility, ventricular stiffness, pulse transit time, resting heart rate, arrhythmia burden, targeted pacing burden, heart rate recovery, impedance, fluid overload, edema, respiration rate, maximum heart rate, ejection fraction, left ventricular pressure, systemic blood pressure, pulmonary artery pressure, blood oxygenation, and presence or concentration of serum biomarkers.

19. The system of claim 18, wherein obtaining rate modification information comprising obtaining the at least one diagnostic parameter of the patient from the pacing device.

20. The system of claim 14, wherein the rate modification information further comprises at least one device configuration, wherein the at least one device configuration comprises one or more of ventricular pacing electrode location, atrial pacing electrode location, and type of pacing therapy.

21. The system of claim 14, wherein the rate modification information further comprises patient-reported information, wherein the patient-reported information comprises one or more of energy level, peripheral edema, desired activity performance, and pacing-related symptoms.

22. The system of claim 14, wherein the rate modification information further comprises patient-reported information, wherein the patient-reported information is obtained from a mobile computing device.

23. The system of claim 14, wherein the computing apparatus is further configured to configuring the pacing device with the lower pacing rate limit.

24. The system of claim 14, wherein obtaining rate modification information comprising obtaining the rate modification information from an electronic medical records system.

25. An implantable medical device comprising:

one or more electrodes to deliver cardiac pacing therapy to and sense electrical activity from a patient's heart; and a computing apparatus operably coupled the one or more electrodes and comprising one or more processors, the computing apparatus configured to:

monitor the patient's intrinsic heart rate using the one or more electrodes;

deliver pacing therapy to the patient's heart in response to the patient's intrinsic rate being less than a lower pacing rate limit;

obtain rate modification information comprising at least one physical characteristic of a patient utilizing a pacing device and at least one diagnostic parameter, the at least one diagnostic parameter comprising a nighttime heart rate;

receive an upper bound, a lower bound, and a percentage of pacing threshold; and determine a lower pacing rate limit for the pacing device based on the obtained rate modification information, the upper bound, the lower bound, and the percentage of pacing threshold, wherein the lower pacing rate limit is increased when a percentage of paced beats exceeds the percentage of pacing threshold.

26. The device of claim 25, wherein the at least one physical characteristic comprises one or more of height, sex, age, body mass index (BMI), body surface area, physical fitness level, and activity level.

27. The device of claim 25, wherein the rate modification information further comprises at least one pathology, wherein the at least one pathology comprises diastolic dysfunction/heart failure with preserved ejection fraction.

28. The device of claim 25, wherein the rate modification information further comprises at least one pathology, wherein the at least one pathology comprises one or more of systolic dysfunction, chronotropic incompetence, worsening heart failure, and comorbid disease.

29. The device of claim 25, wherein the at least one diagnostic parameter further comprises one or more of ventricular contractility, ventricular stiffness, pulse transit time, resting heart rate, arrhythmia burden, targeted pacing burden, heart rate recovery, impedance, fluid overload, edema, respiration rate, maximum heart rate, ejection fraction, left ventricular pressure, systemic blood pressure, pulmonary artery pressure, blood oxygenation, and presence or concentration of serum biomarkers.

30. The device of claim 29, wherein obtaining rate modification information comprising monitoring the at least one diagnostic parameter of the patient using the one or more electrodes.

31. The device of claim 25, wherein the rate modification information further comprises at least one device configuration, wherein the at least one device configuration comprises one or more of ventricular pacing electrode location, atrial pacing electrode location, and type of pacing therapy.

32. The device of claim 25, wherein the rate modification information further comprises patient-reported information, wherein the patient-reported information comprises one or more of energy level, peripheral edema, desired activity performance, and pacing-related symptoms.

33. The device of claim 25, wherein the rate modification information further comprises patient-reported information, wherein the patient-reported information is obtained from a mobile computing device.

* * * * *